(12) United States Patent
Daniel

(10) Patent No.: US 9,757,234 B2
(45) Date of Patent: *Sep. 12, 2017

(54) TOOL ADAPTED FOR INSERTING A PENILE PROSTHESIS INTO A PENIS

(71) Applicant: Coloplast A/S, Humlebaek (DK)

(72) Inventor: Geoffrey A. Daniel, Crystal, MN (US)

(73) Assignee: Coloplast A/S, Humblebaek (DK)

(*) Notice: Subject to any disclaimer, the term of this patent is extended or adjusted under 35 U.S.C. 154(b) by 0 days.

This patent is subject to a terminal disclaimer.

(21) Appl. No.: 15/095,165

(22) Filed: Apr. 11, 2016

(65) Prior Publication Data

US 2016/0220374 A1    Aug. 4, 2016

Related U.S. Application Data

(63) Continuation of application No. 14/253,872, filed on Apr. 16, 2014, now Pat. No. 9,333,079.

(51) Int. Cl.
| | |
|---|---|
| *A61F 2/26* | (2006.01) |
| *A61F 5/41* | (2006.01) |
| *A61B 17/00* | (2006.01) |
| *A61B 17/02* | (2006.01) |
| *A61B 17/04* | (2006.01) |

(52) U.S. Cl.
CPC .............. *A61F 2/26* (2013.01); *A61B 17/00* (2013.01); *A61B 17/02* (2013.01); *A61B 17/0493* (2013.01); *A61F 5/41* (2013.01); *A61F 2005/411* (2013.01)

(58) Field of Classification Search
CPC ........ A61F 2/26; A61F 5/41; A61F 2005/411; A61B 17/00; A61B 17/02; A61B 17/0493
USPC .............................. 600/38–41; 128/897, 898
See application file for complete search history.

(56) References Cited

U.S. PATENT DOCUMENTS

| | | | | |
|---|---|---|---|---|
| 5,484,450 A | * | 1/1996 | Mohamed ................. | A61F 2/26 600/40 |
| 7,066,878 B2 | * | 6/2006 | Eid .......................... | A61F 2/26 600/40 |
| 9,333,079 B2 | * | 5/2016 | Daniel ................... | A61B 17/02 |

* cited by examiner

*Primary Examiner* — Samuel Gilbert
(74) *Attorney, Agent, or Firm* — Coloplast Corp.; Nick Baumann

(57) ABSTRACT

A tool adapted for inserting a penile prosthesis into a penis includes a first neck connected to a first end of a handle and a second neck connected to a second end of a handle, and a first guide connected to the first neck and a second guide connected to the second neck. The first guide has a first cylinder cradle and the second guide has a second cylinder cradle.

15 Claims, 11 Drawing Sheets

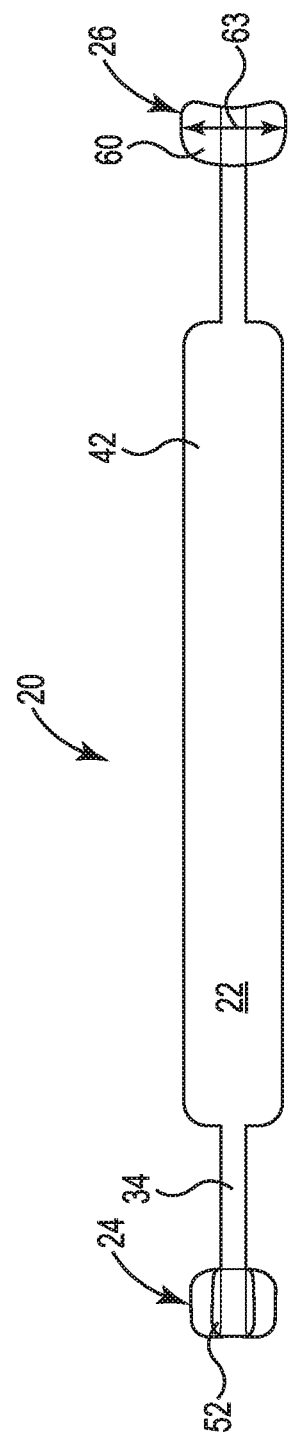

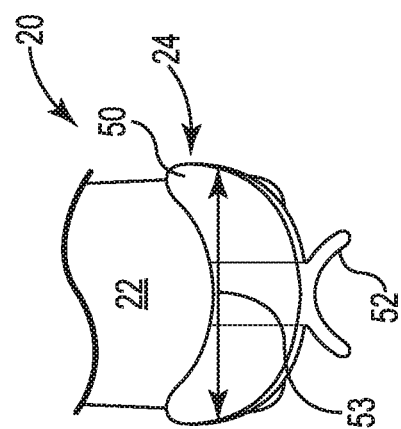
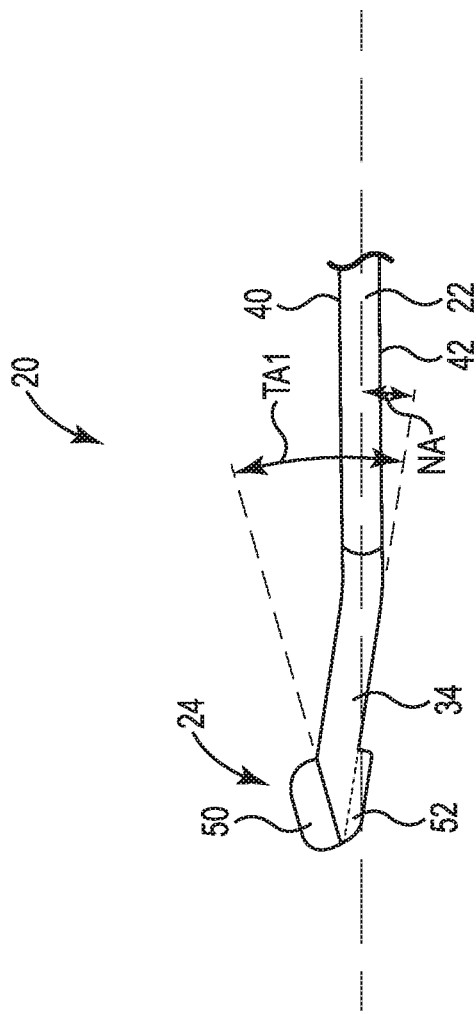

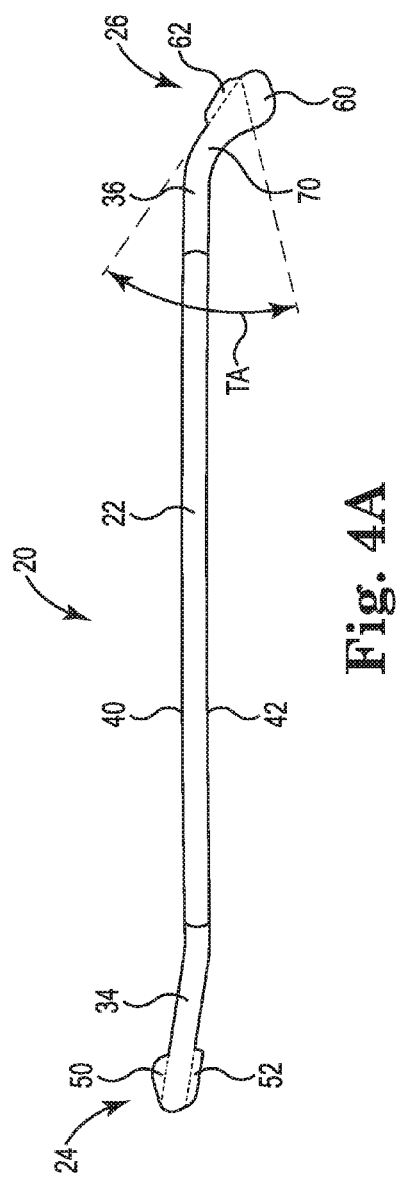
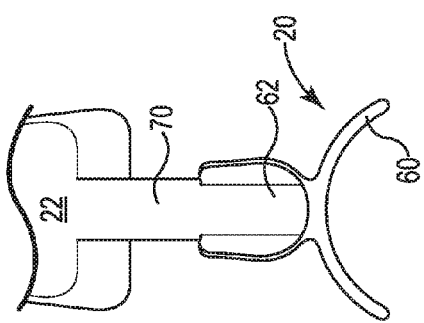
Fig. 4A
Fig. 4B

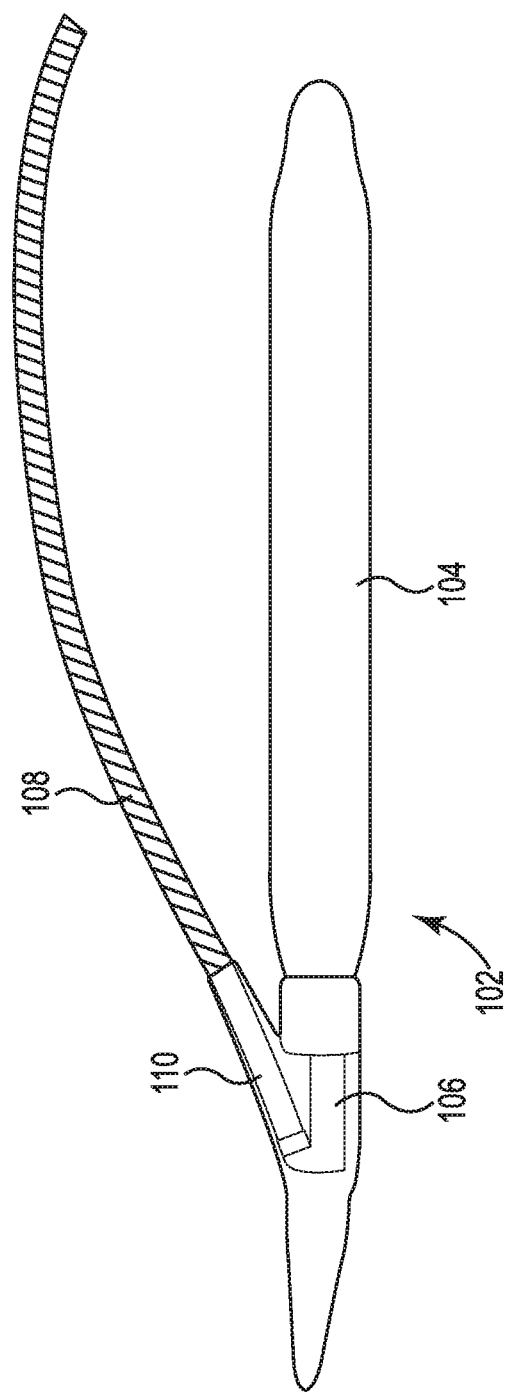

TOOL ADAPTED FOR INSERTING A PENILE PROSTHESIS INTO A PENIS

BACKGROUND

Implanted penile prostheses provide relief for men with erectile dysfunction.

In a typical implantation procedure, the penis of the patient is incised to expose the two corpora cavernosa that are aligned axially in a side-by-side orientation within the penis. Each corpora cavernosum is dilated in a distal direction, for example by introducing gradually larger stainless steel rods into the corpora cavernosum until a space is created that is sized to receive a cylinder of the penile prosthesis. A similar dilation approach is taken in each branch of the crus penis in a proximal direction. Each of the cylinders is inserted into one of the dilated corpora cavernosa with a distal end of the cylinder inserted in the distal direction into the glans penis and a proximal end of the cylinder inserted in the proximal direction into the crus penis.

Although the above-described approach has proven effective in treating erectile dysfunction, surgeons and their staff would welcome improvements in the tools and methods for inserting the proximal end of the cylinder into a narrowed or sclerotic crus penis.

SUMMARY

One aspect provides a tool adapted for inserting a cylinder of a penile prosthesis into a patient. The tool includes a handle extending between first and second guides. The first guide is located at a first end portion of the tool and includes a first cylinder cradle on a first side of the tool and a first tubing cradle on a second side of the tool that is opposite of the first side of the tool. The second guide located at a second end portion of the tool and includes a second cylinder cradle on one of the first side or the second side of the tool and a second tubing cradle on the other side of the tool. The size of the first tubing cradle is the same size as the second tubing cradle and a lateral width of the first cylinder cradle is smaller than a lateral width of the second cylinder cradle.

One aspect provides a tool adapted for inserting a cylinder of a penile prosthesis into a patient. The tool includes a handle, a guide, and a suture protector. The handle extends on a longitudinal axis between a first end of the tool and an opposite second end of the tool. The guide is located at a first end portion of the tool and includes a first cylinder cradle on a first side of the tool and a first tubing cradle on a second side of the tool that is opposite of the first side of the tool. The suture protector is located at a second end portion of the tool. A lateral width of the first tubing cradle is less than a lateral width of the first cylinder cradle.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2C is a bottom view of the tool illustrated in FIG. 1.
FIG. 3A is a side view of a first guide of the tool illustrated in FIG. 1.
FIG. 3B is an end view of the first guide illustrated in FIG. 3A.
FIG. 4A is a side view of a second guide of the tool illustrated in FIG. 1.
FIG. 4B is an end view of the second guide illustrated in FIG. 4A.
FIG. 5B is a side view of the cylinder illustrated in FIG. 5A.

DETAILED DESCRIPTION

Figure 1:
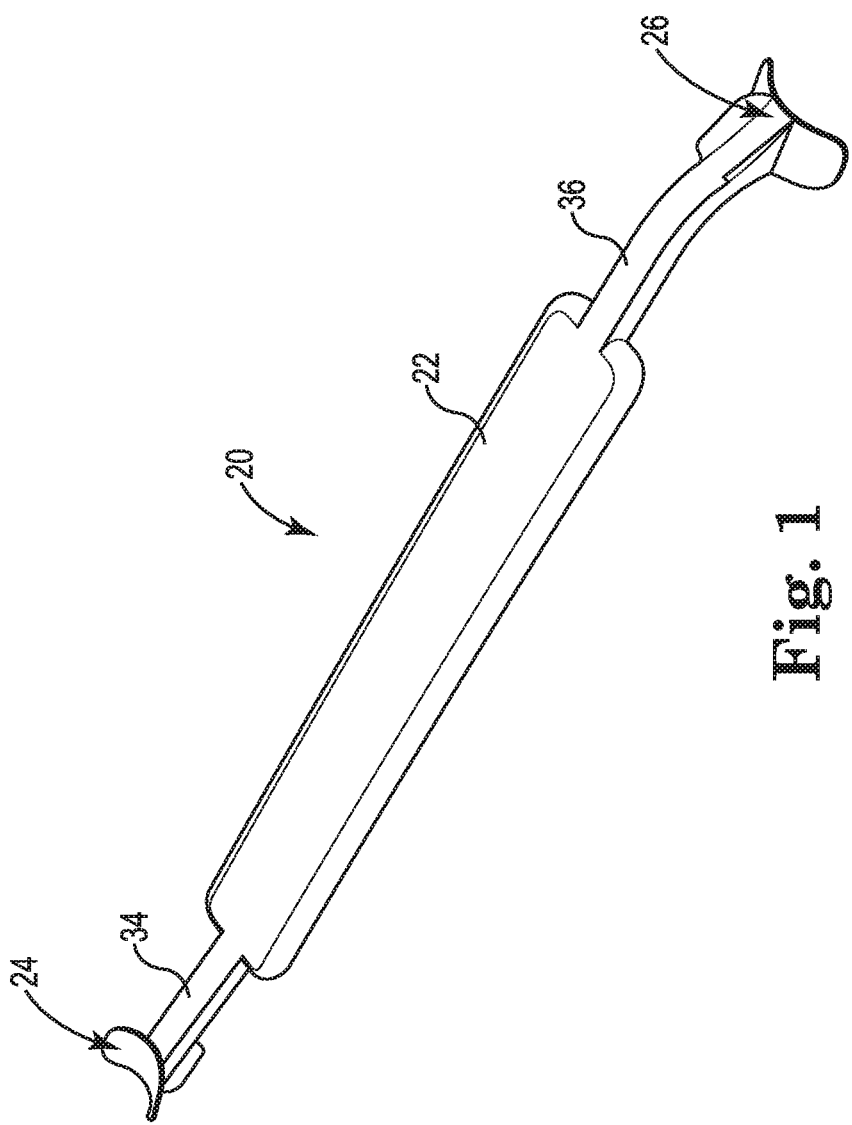
FIG. 1 is a perspective view of one embodiment of a tool adapted for inserting a cylinder of a penile prosthesis into a patient.

In the following Detailed Description, reference is made to the accompanying drawings that are a part of this application and illustrate various embodiments. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the invention. The following detailed description is not to be taken in a limiting sense, and the scope of the invention is defined by the appended claims.

The features of the various exemplary embodiments described in this application may be combined with each other ("mixed and matched"), unless specifically noted otherwise.

Soft tissue includes dermal tissue, sub-dermal tissue, ligaments, tendons, or membranes but does not include bone.

The term "proximal" in this application means that part that is situated next to or near the point of attachment or origin or a central point; for example, as located toward a center of the human body. The crus penis is proximal relative to the patient.

The term "distal" in this application means that part that is situated away from the point of attachment or origin or the central point; for example, as located away from the center of the human body. The glans penis is distal relative to the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12 inch ruler has a center point at 6 inches, a first end at zero inches and a second, opposite end at 12 inches, an end portion from 1 inch to the first end and another end portion from 11 inches to the second end.

Tubing angle means an angular dimension measured between a surface of a rear proximal tip of a cylinder of a penile prosthesis and a surface of tubing that extends away from the rear proximal tip. Some cylinders manufactured by Coloplast of Minneapolis, Minn. are termed "zero degree tubing" cylinders and have a tubing angle of about zero degrees. Other cylinders manufactured by Coloplast have tubing angles of 22.5 degrees or 45 degrees, depending upon the application.

Shallow tubing angle means a cylinder of a penile prosthesis having a tubing angle between the tubing and the cylinder in a range from 0-35 degrees.

Broad tubing angle means a cylinder of a penile prosthesis having a tubing angle between the tubing and the cylinder in a range from 35-70 degrees.

The typical penile prosthesis is implanted after suitably dilating the corpora cavernosa and the crus penis with a cavernatome or other dilation tool. Recently, surgeons have indicated a preference for implanting the proximal tip of the cylinder into the crus penis, when possible, without relying upon rear tip extenders or other parts added to the cylinder. A cylinder of the prosthesis is inserted into one of the corpora cavernosa by passing a needle/suture through the glans penis to direct/pull a distal end of the cylinder distally through the corpora cavernosum and into the glans penis. The proximal end of the cylinder is inserted and forced into the crus penis in an attempt to fully seat the cylinder in the crus at the root of the penis. Some patients have a well defined crus penis that is readily dilated to accept a standard diameter proximal tip of a cylinder. The surgeon will at times employ a forceps or other available tool to insert the proximal tip of the cylinder fully and completely into the well-dilated crus penis.

Some patients have developed sclerosis in the crus penis that hinders the surgeon in fully seating the cylinder into the root of the penis. One solution to the issue of patients that present with sclerosis of the crus penis is to implant a cylinder having a narrower proximal tip than the standard diameter proximal tip. Surgeons have at times employed a forceps or other available tool to push the proximal tip of the cylinder fully and completely into the crus penis. However, this approach has the potential to undesirably perforate the wall of the inflatable cylinder, particularly when the crus penis has proven difficult to dilate.

Embodiments provide a tool that is suited for properly seating the proximal tip of either an updated narrow cylinder or a standard broad cylinder into the crus penis. The tool is configured to provide excellent engagement with the proximal tip at a location where the tubing extends from the cylinder. The tool has a first engagement surface that cradles a portion of the cylinder and a second engagement surface that cradles a portion of the tubing. The combination of the engagement with these two surfaces of the cylinder results in a tool that achieves excellent engagement with the cylinder, which allows the tool to fully seat either a narrow cylinder or a broad cylinder deep into the crus penis.

FIG. 1 is a perspective view of one embodiment of a tool 20 adapted for inserting a cylinder of a penile prosthesis into a patient. The tool 20 includes a handle 22 extending between a first guide 24 on a first end portion of the tool and a second guide 26 on a second end portion of the tool. In one embodiment, the first guide 24 is different from the second guide 26, where the first guide 24 is sized for insertion of a cylinder having a shallow tubing angle and the second guide 26 is sized for insertion of a cylinder having a broad tubing angle. In one embodiment, the first guide 24 is different from the second guide 26, where the first guide 24 is sized for insertion of a narrow cylinder and the second guide 26 is sized for insertion of a standard broad cylinder. In this manner, the tool 20 is a combination tool well-suited for inserting cylinders of different sizes (depending upon the patient's anatomy) into the crus penis.

In one embodiment, the handle 22 provides a wide ergonomic surface to allow for optimum control and the tool 20 includes a first neck 34 extending between the handle 22 and the first guide 24 and a second neck 36 extending between the handle 22 and the second guide 26. It is usually desirable for the first neck 34 to be narrower than the handle 22 and for the second neck 36 to likewise be narrower than the handle 22.

Figure 2A:
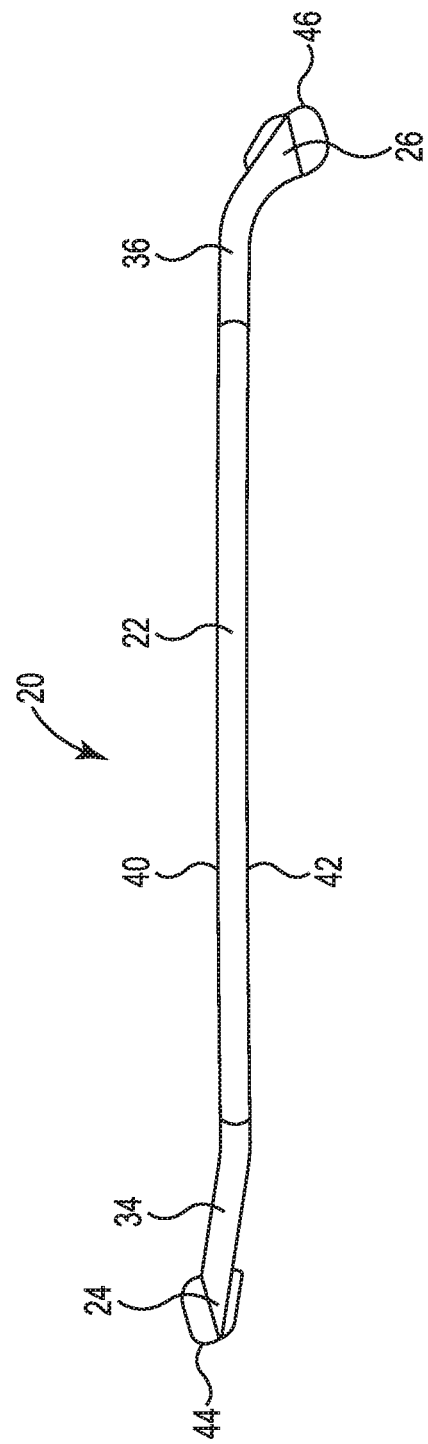
FIG. 2A is a side view of the tool illustrated in FIG. 1.

FIG. 2A is a side view of the tool 20. The tool 20 includes a first surface 40 (or a top surface 40) and a second surface 42 (or a bottom surface 42). The first guide 24 is located at a first end portion that defines a first end 44 of the tool 20 and the second guide 26 is located at a second end portion that defines a second end 46 of the tool 20.

Figure 2B:
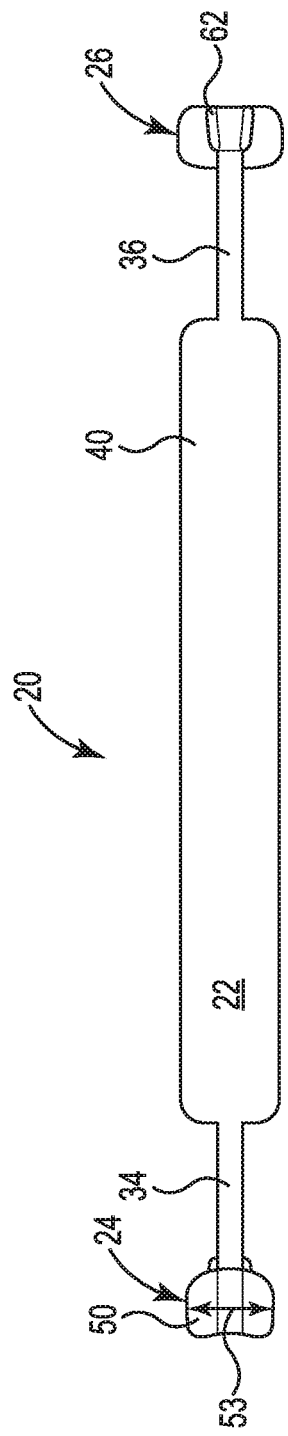
FIG. 2B is a top view of the tool illustrated in FIG. 1.

FIG. 2B is a top view and FIG. 2C is a bottom view of the tool 20. The first guide 24 includes a first cylinder cradle 50 located on the top surface 40 of the tool 20 and a first tubing cradle 52 located on the bottom surface 42 of the tool 20. The second guide 26 includes a first cylinder cradle 60 located on the bottom surface 42 of the tool 20 and a second tubing cradle 62 located on the top surface 40 of the tool 20. With reference to FIG. 2B and FIG. 2C, the first guide 24 presents the first cylinder cradle 50 on the top surface 40 of the tool 20 and the second guide 26 presents the second cylinder cradle 60 on the bottom surface 42 of the tool 20. Thus, in the illustrated embodiment, the first cylinder cradle 50 is on an opposite side of the tool 20 from the second cylinder cradle 60. However, other orientations of the cylinder cradles 50, 60 are also acceptable including placement of both cradles on the same surface of the tool 20.

In one embodiment, a size of the first tubing cradle 52 is substantially equal to a size of the second tubing cradle 62, which configures the cradles 52, 62 for engagement with the kink resistant tubing employed with penile prosthetic cylinders. As an example, each of the tubing cradles 52, 62 has about the same lateral width, and the lateral width is sized to receiving tubing having a width of about 5 mm in diameter. In one embodiment, a lateral width 53 of the first cylinder cradle 50 (FIG. 2B) is smaller (or narrower) than a lateral width 63 of the second cylinder cradle 60 (FIG. 2C), which configures the first cylinder cradle 50 for engagement with narrow cylinders and configures the second cylinder cradle 60 for engagement with the standard, wider cylinders.

FIG. 3A is a side view and FIG. 3B is an end view of the first guide 24. In one embodiment, the first guide 24 is sized for insertion of a cylinder provided with a shallow tubing angle and includes a tubing angle TA1 between the first cylinder cradle 50 and the first tubing cradle 52 that is in a range between 0-35 degrees. One suitable tubing angle TA1 between the first cylinder cradle 50 and the first tubing cradle 52 is selected to be 22.5 degrees and is sized to accommodate a cylinder having shallow tubing angle. The tubing angle TA1 and the lateral width 53 of the first cylinder cradle 50 adapts the first guide 24 for engagement with narrow cylinders having shallow tubing angles.

In one embodiment, the neck 34 extending between the handle 22 and the first guide 24 is oriented at a non-zero neck angle NA relative to the handle 22 in a range from 0-45 degrees.

FIG. 4A is a side view of the tool 20 and FIG. 4B is an end view of the second guide 26. In one embodiment, the second guide 26 is sized for insertion of a cylinder provided with a broad tubing angle and includes a tubing angle TA between the second cylinder cradle 60 and the second tubing cradle 62 that is in a range between 35-70 degrees. One suitable tubing angle TA between the second cylinder cradle 60 and the second tubing cradle 62 is selected to be 45 degrees and is sized to accommodate a cylinder having a broad tubing angle. The broad tubing angle TA and the lateral width 63 of the second cylinder cradle 60 adapts the second guide 26 for engagement with standard diameter cylinders having broad tubing angles.

In one embodiment, the neck 36 extending between a handle 22 and the second guide 26 is oriented at an angle of about 0 degrees relative to the handle 22.

In one embodiment, the tool 20 includes a curved extension member 70 connected between the second neck 36 and the second guide 26 such that the second guide 26 is elevated or offset a distance away from the second side 42 of the tool 20.

The tool 20 is suitably provided as a sterile, single use, disposable tool. Suitable materials for fabricating the tool 20 include plastics or metal. Suitable plastics for fabricating the tool 20 include polyethylene, high density polyethylene, polypropylene, acrylonitrile butadiene styrene (ABS), polyurethane, or the like. Fabricating the tool 20 from titanium or stainless steel is also acceptable.

Figure 5A:
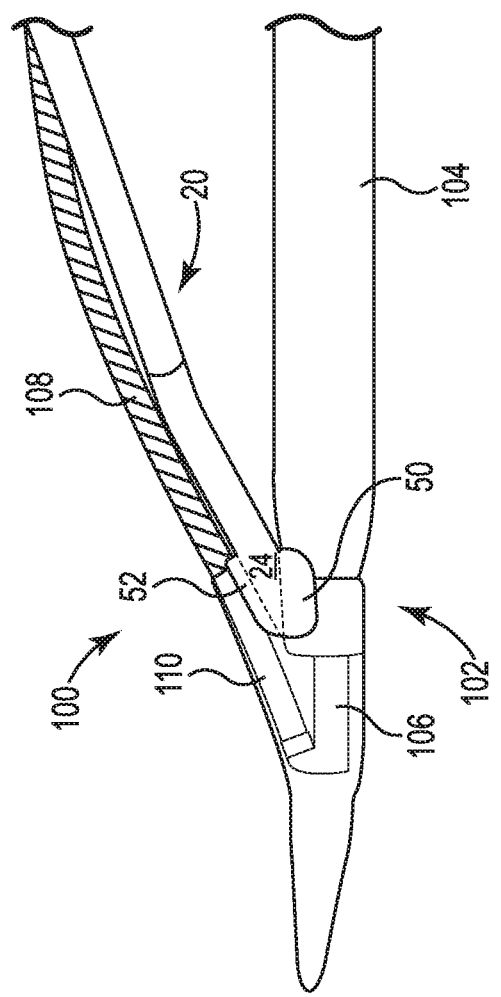
FIG. 5A is a side view of one embodiment of a penile prosthesis system including the tool illustrated in FIG. 1 engaged with a cylinder of a penile prosthesis.

FIG. 5A is a side view of one embodiment of a penile prosthesis system 100 including the tool 20 engaged with a cylinder 102 of a penile prosthesis. FIG. 5B is a side view of the cylinder 102.

A penile prosthesis usually includes a reservoir containing an amount of liquid, a pump provided to transfer the liquid to and from the cylinder, and two implantable cylinders (one for each corpora cavernosum). One suitable penile prosthesis is the Titan® OTR penile prosthesis that is provided with a one-touch release (OTR) pump, a reservoir, and two cylinders (either of standard diameter or of a narrow diameter). The Titan® OTR penile prosthesis is available from Coloplast Corp., Minneapolis, Minn.

The cylinder 102 includes an inflatable portion 104 connected to a proximal tip 106, and tubing 108 connected to the proximal tip 106 at a tubing junction 110. The cylinder 102 is of a style referred to as a narrow cylinder where the inflatable portion 104 has a diameter of about 12 mm prior to inflation and the tubing junction 110 forms a shallow tubing angle of about 22.5 degrees relative to the proximal tip 106. The first guide 24 of the tool 20 is engaged between the proximal tip 106 and the tubing junction 110. In particular, the first cylinder cradle 50 receives a portion of the proximal tip 106 and the first tubing cradle 52 engages with the tubing junction 110. In this manner, the first guide 24 is controllably and positively engaged with the cylinder 102, which allows the surgeon to seat the proximal tip 106 fully and completely into the dilated crus penis, even if the crus is sclerotic.

Figure 6:
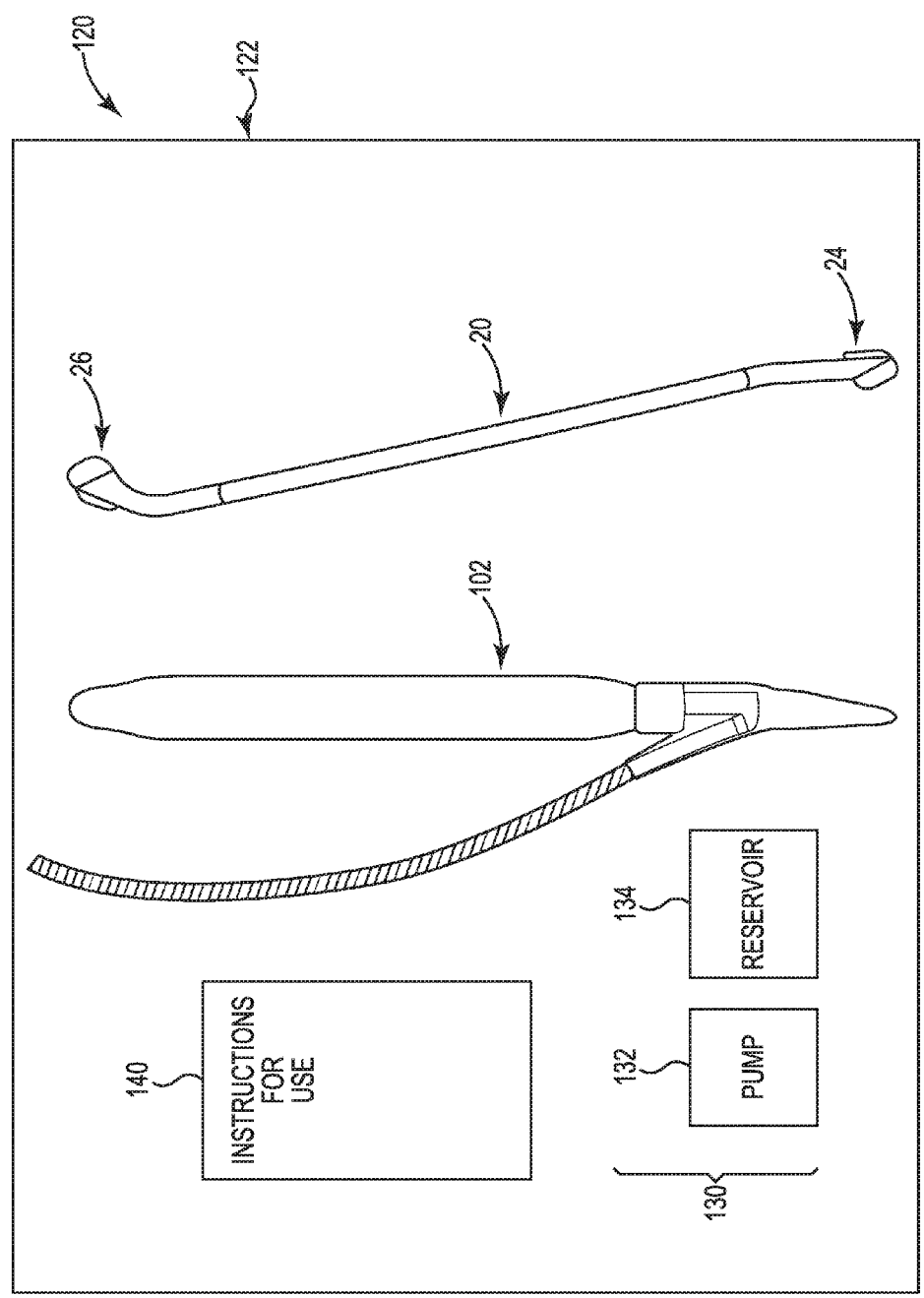
FIG. 6 is a top view of one embodiment of a kit of parts.

FIG. 6 is a top schematic view of one embodiment of a kit 120 of parts. The kit 120 of parts includes packaging 122 containing a penile prosthesis 130, a tool 20 useful for implanting a portion of the penile prosthesis, and instructions 140 for use. The penile prosthesis 130 includes a pump 132 and a reservoir 134 that are adapted to be connected to the cylinder 102. The reservoir 134 contains a volume of liquid that is moved by the pump 132 into the cylinder 102 to inflate the cylinder and provide the patient with an erection. The tool 20 is the tool described above and includes a first guide 24 and a second guide 26 that are each sized to accommodate various sizes and configurations of cylinders. The instructions 140 for use describe procedures for inserting the proximal tip 106 of the cylinder 102 with the tool 20 into the crus penis.

In one embodiment, the kit 120 of parts includes the packaging 122 described above containing the penile prosthesis 130, a tool 200 described below that is provided with a suture protector 206, and instructions 140 for use in implanting the prosthesis 130 and in closing the incision with the suture protector 206.

Figure 7:
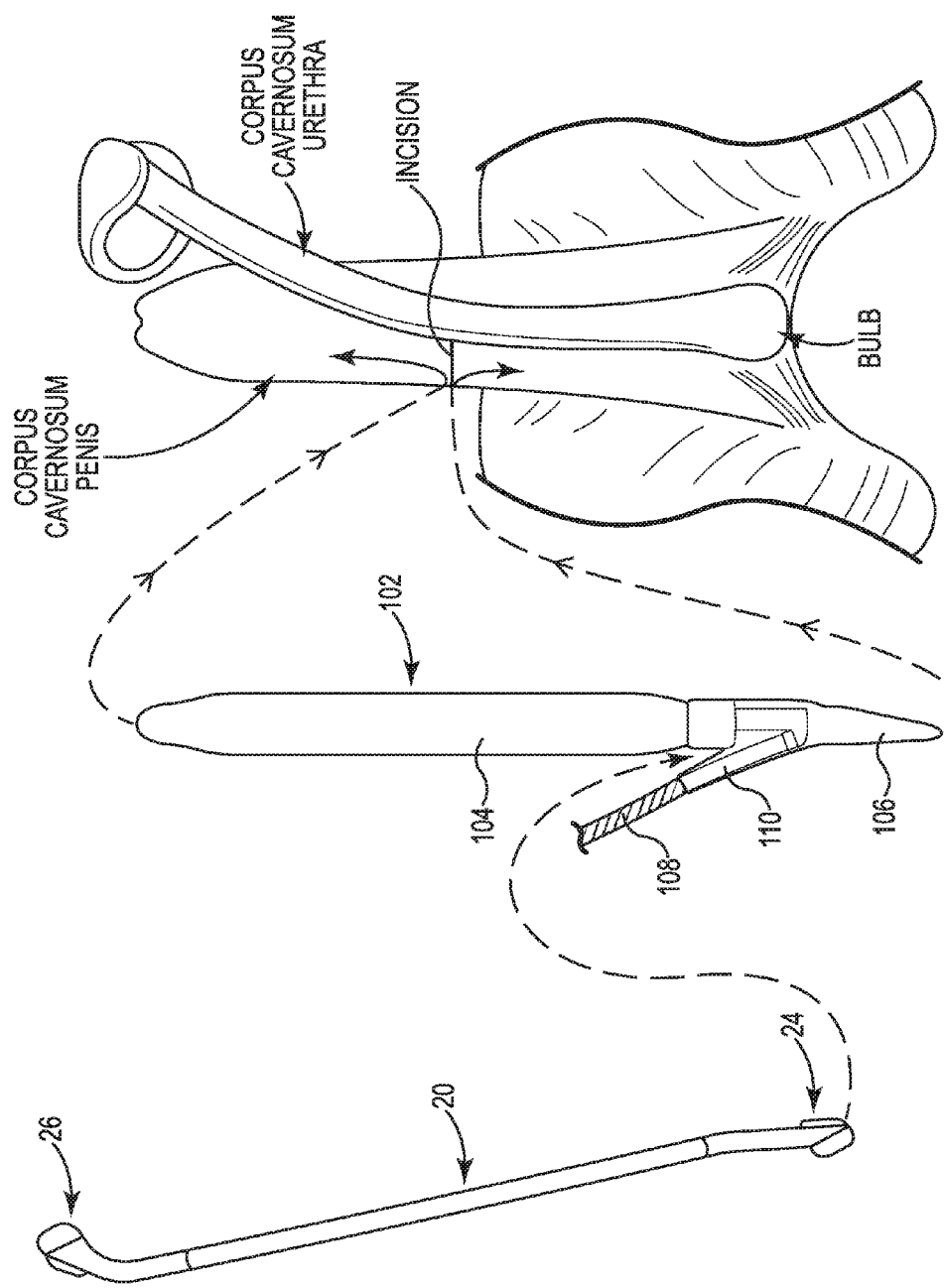
FIG. 7 is a schematic view of one embodiment of a penile prosthesis system employed in treating erectile dysfunction.

FIG. 7 is a schematic view of one embodiment of the penile prosthesis system 100 readied for implantation in treatment of erectile dysfunction.

The patient is suitably prepped for surgery and an incision is formed in the penis. The surgeon selects the appropriate incision, for example a penis-scrotal incision or another incision selected by the surgeon. Each corpus cavernosa of the penis is dilated in a distal direction, and the crus penis is dilated in a proximal direction. The distal tip of the cylinder 102 is directed through the incision in a distal direction along the dilated corpus cavernosum in the penis. The proximal tip 106 of the cylinder 102 is inserted into the crus penis by engaging the first guide 24 of the tool 20 between the tubing junction 110 and the cylinder 104. The first guide 24 fully engages with the region between the tubing junction 110 and the cylinder 104 to provide excellent leverage in inserting the proximal tip 106 into the crus penis.

Subsequent to inserting the cylinder 102 into the penis, the pump 132 and the reservoir 134 (FIG. 6) are implanted into the patient. The pump 132 is desirably implanted into the scrotum, and the reservoir 134 is desirably implanted into a location in the abdomen, or other locations as selected by the surgeon. The pump 132 and the reservoir 134 are suitably connected to the tubing 108 of the cylinder 102 and the incisions are closed.

Figure 8:
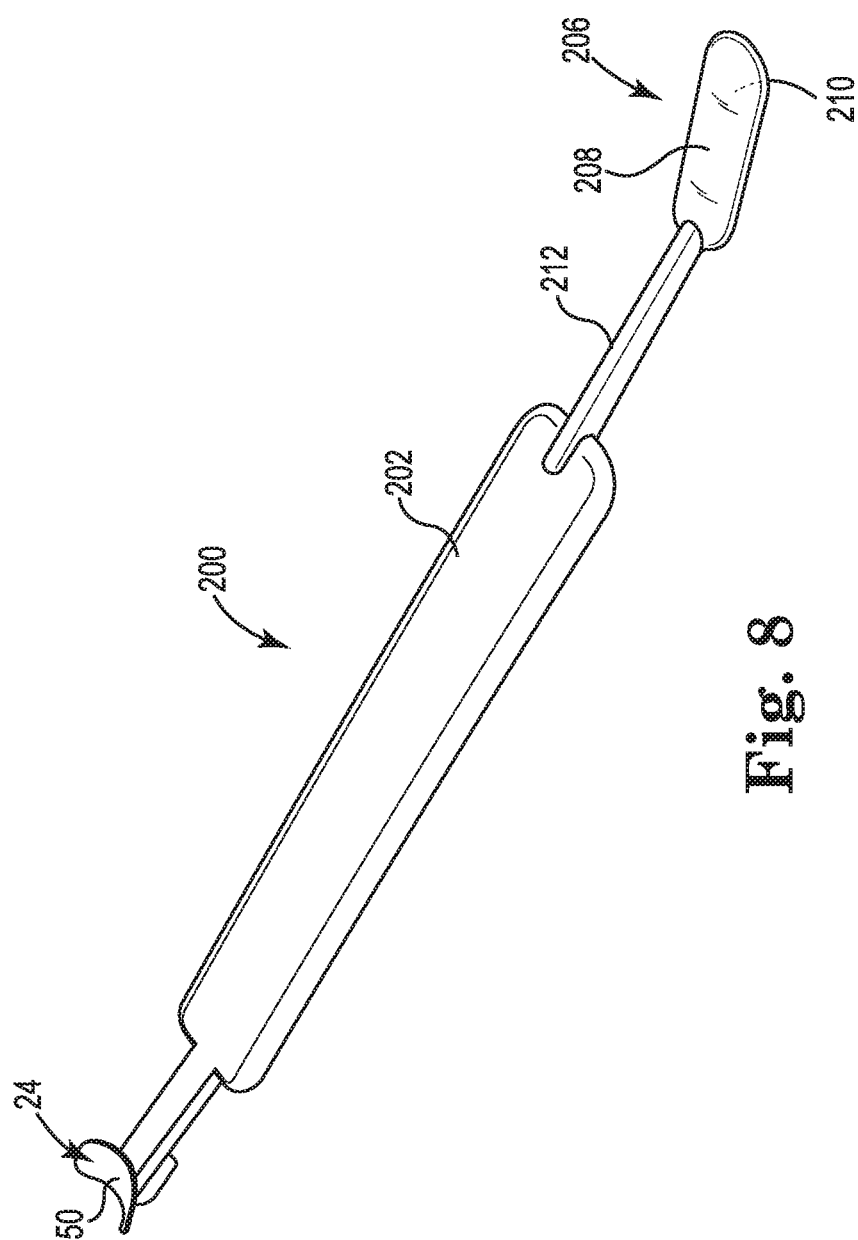
FIG. 8 is a perspective view of one embodiment of a tool adapted for inserting a cylinder of a penile prosthesis into a patient.

FIG. 8 is a perspective view of one embodiment of a tool 200 adapted for inserting a cylinder of a penile prosthesis into a patient and closing the incision formed to place the cylinder in the penis. The tool 200 includes a handle 202 extending between the first guide 24 on the first end portion of the tool and a suture protector 206 formed on a second end portion of the tool. The first guide 24 is as described above. The suture protector 206 is provided for placement between the skin of the penis and the cylinder implanted in the penis and functions to reduce the opportunity for the surgeon or other professional from undesirably contacting the inflatable cylinder with a suturing needle during closure of the incision.

The suture protector 206 includes a flat suture plate 208 on a first side and a curved face 210 on a side opposite of the flat suture plate 208. The curved face 201 has a shape and curvature similar to the first cylinder cradle 50 of the first guide 24. In one embodiment, a narrow neck 212 is connected between the handle 202 and the suture protector 206. The narrow neck 212 is sized to take up a minimum of space as the suture protector 206 is inside of the incision.

With additional reference to FIG. 7, after placement of the cylinder 102 into the penis, the surgeon inserts the suture protector 206 into the incision and engages the curved face 210 with the inflatable portion 104 of the cylinder 102. The surgeon closes the incision in an appropriate manner up to a location near the narrow neck 212. Thereafter, the surgeon removes the suture protector 206 from the substantially closed incision and ties off the suture line.

Embodiments provide a tool that is suited for properly seating the proximal tip of either a narrow cylinder or a standard broad cylinder into the crus penis, whether the crus suffers from sclerosis or not. The tool provides excellent engagement with the proximal tip by cradling a portion of the cylinder and a portion of the tubing. The combination of the engagement of these two surfaces results in a tool that achieves excellent engagement with the cylinder, which allows the tool to fully seat either a narrow cylinder or a broad cylinder deep into the crus penis.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A tool adapted for inserting a penile prosthesis into a penis, the tool comprising:
    a handle having a first end, an opposite second end, and opposed lateral sides that are oriented in a plane;
    a first neck connected to the first end of the handle and a second neck connected to the second end of the handle, with the first neck oriented at a non-zero angle relative to the plane and the second neck planar with the handle and oriented at an angle of zero degrees relative to the plane; and
    a first guide connected to the first neck and a second guide connected to the second neck, with the first guide including a first cylinder cradle formed on a first side of the tool and integrated with a first tubing cradle that is formed on an opposing second side of the tool and the second guide having a second cylinder cradle and a second tubing cradle;
    wherein a lateral width of the first cylinder cradle is smaller than a lateral width of the second cylinder cradle.

2. The tool of claim 1, wherein a width of each of the first neck and the second neck is less than a lateral width of the handle.

3. The tool of claim 1, wherein a width of the first neck is less than a lateral width of the first tubing cradle and less than the lateral width of the first cylinder cradle.

4. The tool of claim 1, wherein a lateral width of the first tubing cradle is equal to a lateral width of the second tubing cradle.

5. The tool of claim 1, wherein the second cylinder cradle is formed on the first side of the tool and the second tubing cradle formed on the second side of the tool.

6. The tool of claim 1, wherein the handle is oriented in the plane to define a top side of the handle opposite from a bottom side of the handle, with the first cylinder cradle oriented at the top side of the handle and the second cylinder cradle oriented at the bottom side of the handle.

7. The tool of claim 1, wherein the first guide is configured for use with a penile prosthetic having a shallow tubing angle in which an angle between the first cylinder cradle and the first tubing cradle is in a range of 0-35 degrees and the second guide is configured for use with a penile prosthetic having a broad tubing angle in which an angle between the second cylinder cradle and the second tubing cradle is in a range of 35-70 degrees.

8. The tool of claim 1, further comprising:
    a curved extension member connected between the second neck and the second guide such that the second guide is elevated a distance away from the plane of the handle.

9. The tool of claim 1, wherein the second cylinder cradle is formed on the second side of the tool and the second tubing cradle formed on the first side of the tool.

10. A tool adapted for inserting a penile prosthesis into a penis, the tool comprising:
    a handle having a first end, an opposite second end, and opposed lateral sides that are oriented in a plane;
    a first neck connected to the first end of the handle and a second neck connected to the second end of the handle; and
    a first guide connected to the first neck and a second guide connected to the second neck, with the first guide integrated to provide a first cylinder cradle and a separate first tubing cradle and the second guide integrated to provide a second cylinder cradle and a separate second tubing cradle;
    wherein a curved extension member is connected between the second neck and the second guide such that the second guide is elevated a distance away from the plane of the handle.

11. The tool of claim 10, wherein the first neck is oriented at a non-zero angle relative to the plane of the handle and the second neck is planar with the handle and oriented at an angle of zero degrees relative to the plane of the handle.

12. The tool of claim 10, wherein the first cylinder cradle is concave and the first tubing cradle is concave.

13. The tool of claim 10, wherein the first cylinder cradle is concave and the second cylinder cradle is concave.

14. The tool of claim 10, wherein a lateral width of the first cylinder cradle is smaller than a lateral width of the second cylinder cradle.

15. A tool adapted for inserting a penile prosthesis into a penis, the tool comprising:
    a handle having a first end, an opposite second end, and opposed lateral sides that are oriented in a plane;
    a first neck connected to the first end of the handle and a second neck connected to the second end of the handle; and
    a first guide connected to the first neck and a second guide connected to the second neck, with the first guide having a first cylinder cradle and the second guide having a second cylinder cradle;
    wherein the first neck is oriented at a non-zero angle relative to the plane of the handle and the second neck is planar with the handle and oriented at an angle of zero degrees relative to the plane of the handle;
    wherein a curved extension member is connected between the second neck and the second guide such that the second guide is elevated a distance away from the plane of the handle.

* * * * *